US00RE43767E

(19) United States
(12) Reissued Patent
Eggers et al.

(10) Patent Number: US RE43,767 E
(45) Date of Reissued Patent: Oct. 23, 2012

(54) CONTROL OF DATA TRANSMISSION BETWEEN A REMOTE MONITORING UNIT AND A CENTRAL UNIT

(75) Inventors: Philip N. Eggers, Satl Lake City, UT (US); Lon M. Severe, San Diego, CA (US)

(73) Assignee: CardioNet, Inc., Conshohocken, PA (US)

(21) Appl. No.: 12/774,026

(22) Filed: May 5, 2010

Related U.S. Patent Documents

Reissue of:
(64) Patent No.: 6,694,177
Issued: Feb. 17, 2004
Appl. No.: 09/841,152
Filed: Apr. 23, 2001

(51) Int. Cl.
*A61B 5/04* (2006.01)

(52) U.S. Cl. ..... 600/509; 600/300

(58) Field of Classification Search ..... 600/508–527, 600/344, 372, 382–394, 481–485, 493, 300; 607/30–32, 60; 128/902–903
See application file for complete search history.

(56) References Cited

U.S. PATENT DOCUMENTS

| | | | | |
|---|---|---|---|---|
| 3,478,344 | A | 11/1969 | Schwitzgebel et al. | 340/312 |
| 3,768,014 | A | 10/1973 | Smith et al. | 324/158 R |
| 3,885,552 | A | 5/1975 | Kennedy | 128/2.05 R |
| 3,902,478 | A | 9/1975 | Konopasek et al. | 128/2.06 F |
| 3,925,762 | A | 12/1975 | Keitlinger et al. | 340/150 |
| 4,173,971 | A | 11/1979 | Karz | 128/702 |
| 4,183,354 | A | 1/1980 | Sibley et al. | 128/711 |
| 4,211,237 | A | 7/1980 | Nagel | 128/698 |
| 4,230,127 | A | 10/1980 | Larson | 128/706 |
| 4,241,237 | A | 12/1980 | Paraskevakos et al. | 179/2 AM |
| 4,457,315 | A | 7/1984 | Bennish | 128/704 |
| 4,531,527 | A | 7/1985 | Reinhold, Jr. et al. | 128/696 |

(Continued)

FOREIGN PATENT DOCUMENTS

DE 44 41 907 6/1995

(Continued)

OTHER PUBLICATIONS

Litigation search for USPN 6,694,177.*

(Continued)

*Primary Examiner* — Mark W Bockelman
(74) *Attorney, Agent, or Firm* — Fish & Richardson P.C.

(57) ABSTRACT

A patient is monitored using a monitoring apparatus including a remote monitoring unit associated with the patient and having a sensor that measures a physiological characteristic of the patient, a central unit, and a communications device which selectively establishes a communications link between the remote monitoring unit and the central unit. The remote monitoring unit obtains a monitored data set for the patient, analyzes the monitored data set to obtain a derived data set from the monitored data set, and determines from the derived data set that communication with the central unit is required. A communications link is established with the central unit, and the remote monitoring unit transmits to the central unit an initially transmitted data set related to the monitored data set. The central unit analyzes the initially transmitted data set and instructs the remote monitoring unit as to any additional transmitted data set related to the monitored data set that is to be transmitted from the remote monitoring unit to the central unit and a time at which the additional transmitted data set is to be transmitted.

25 Claims, 2 Drawing Sheets

U.S. PATENT DOCUMENTS 4,535,783 A 8/1985 Marangoni ..... 128/711
4,598,272 A 7/1986 Cox ..... 340/539
4,622,979 A 11/1986 Katchis et al.
4,630,204 A 12/1986 Mortara
4,651,157 A 3/1987 Gray et al. ..... 342/457
4,675,656 A 6/1987 Narcisse ..... 340/539
4,706,689 A 11/1987 Man ..... 128/903
4,742,357 A 5/1988 Rackley ..... 342/457
4,750,197 A 6/1988 Denekamp et al. ..... 379/58
4,777,478 A 10/1988 Hirsch et al. ..... 340/573
4,785,291 A 11/1988 Hawthorne ..... 340/573
4,819,860 A 4/1989 Hargrove et al. ..... 228/668
4,920,489 A 4/1990 Hubelbank et al.
4,938,228 A 7/1990 Righter et al.
4,951,681 A 8/1990 Mortara
4,952,928 A 8/1990 Carroll et al. ..... 340/825.54
4,958,641 A 9/1990 Digby et al.
4,974,607 A 12/1990 Miwa
4,977,899 A 12/1990 Digby et al.
5,003,984 A 4/1991 Muraki et al. ..... 128/710
5,113,869 A 5/1992 Nappholz et al. ..... 128/696
D326,716 S 6/1992 Mortara
5,172,698 A 12/1992 Stanko ..... 128/697
5,191,891 A 3/1993 Righter
5,197,479 A 3/1993 Hubelbank et al.
5,223,844 A 6/1993 Mansell et al. ..... 342/357
5,226,425 A 7/1993 Righter
5,301,105 A 4/1994 Cummings, Jr. ..... 364/401
5,309,920 A 5/1994 Gallant et al. ..... 128/710
5,311,197 A 5/1994 Sorden et al. ..... 342/457
5,318,592 A 6/1994 Schaldach ..... 607/5
5,321,618 A 6/1994 Gessman ..... 364/413.06
5,334,974 A 8/1994 Simms et al. ..... 340/990
5,335,664 A 8/1994 Nagashima ..... 128/696
5,336,245 A 8/1994 Adams et al. ..... 607/32
5,348,008 A 9/1994 Bornn et al.
5,365,935 A 11/1994 Righter et al.
5,389,934 A 2/1995 Kass ..... 342/357
5,394,879 A 3/1995 Gorman ..... 128/707
5,418,537 A 5/1995 Bird ..... 342/356
5,421,342 A 6/1995 Mortara
5,422,816 A 6/1995 Sprague et al. ..... 364/449
5,423,869 A 6/1995 Poore et al. ..... 607/18
5,458,123 A 10/1995 Unger ..... 128/696
5,461,365 A 10/1995 Schlager et al. ..... 340/573
5,470,233 A 11/1995 Fruchterman et al. ..... 434/112
5,479,482 A 12/1995 Grimes ..... 379/59
5,487,755 A 1/1996 Snell et al. ..... 607/27
5,490,515 A 2/1996 Mortara
5,497,149 A 3/1996 Fast ..... 340/988
5,503,158 A 4/1996 Coppock et al. ..... 128/696
5,504,491 A 4/1996 Chapman ..... 342/357
5,515,419 A 5/1996 Sheffer ..... 379/58
5,522,396 A 6/1996 Langer et al.
5,544,661 A 8/1996 Davis et al.
5,546,950 A 8/1996 Schoeckert et al.
5,549,113 A 8/1996 Halleck et al. ..... 128/671
5,564,429 A 10/1996 Bornn et al. ..... 128/696
5,568,814 A 10/1996 Gallant et al. ..... 128/672
5,573,506 A 11/1996 Vasko ..... 604/65
5,576,952 A 11/1996 Stutman et al.
5,579,775 A 12/1996 Dempsey et al. ..... 128/670
5,581,369 A 12/1996 Righter et al.
D377,983 S 2/1997 Sabri
5,617,871 A 4/1997 Burrows ..... 128/696
5,620,472 A 4/1997 Rahbari ..... 607/27
5,626,624 A 5/1997 Schaldach et al. ..... 607/24
5,626,630 A 5/1997 Markowitz et al. ..... 607/60
5,629,678 A 5/1997 Gargano et al. ..... 340/573
5,634,468 A 6/1997 Platt et al.
5,649,303 A 7/1997 Hess et al. ..... 455/63
5,652,570 A 7/1997 Lepkofker ..... 340/573
5,678,562 A 10/1997 Sellers
5,704,351 A 1/1998 Mortara et al.
5,704,364 A 1/1998 Saltzstein et al. ..... 128/696
5,704,366 A 1/1998 Tacklind et al. ..... 128/716
5,713,856 A 2/1998 Eggers et al. ..... 604/65
5,720,770 A 2/1998 Nappholz et al. ..... 607/30
5,720,771 A 2/1998 Snell ..... 607/60
5,724,025 A 3/1998 Tavori ..... 340/573
5,729,197 A 3/1998 Cash ..... 340/539
5,730,143 A 3/1998 Schwarzberg
5,731,757 A 3/1998 Layson, Jr. ..... 340/573
5,748,103 A 5/1998 Flach et al. ..... 340/870.07
5,749,367 A 5/1998 Gamlyn et al. ..... 128/696
5,749,907 A 5/1998 Mann ..... 607/27
5,752,976 A 5/1998 Duffin et al. ..... 607/32
5,759,199 A 6/1998 Snell et al. ..... 607/60
5,882,300 A 3/1999 Malinouskas et al. ..... 600/300
5,891,169 A 4/1999 Boheim et al. ..... 607/4
5,913,827 A 6/1999 Gorman ..... 600/509
5,913,881 A 6/1999 Benz et al. ..... 607/36
5,931,791 A 8/1999 Saltzstein et al.
5,941,829 A 8/1999 Saltzstein et al. ..... 600/509
5,944,659 A 8/1999 Flach et al. ..... 600/300
5,950,110 A 9/1999 Hendrickson ..... 455/1
5,959,529 A 9/1999 Kail, IV
D414,870 S 10/1999 Saltzstein et al.
5,964,794 A 10/1999 Bolz et al. ..... 607/121
5,966,692 A 10/1999 Langer et al.
5,970,986 A 10/1999 Bolz et al. ..... 128/899
5,987,352 A 11/1999 Klein et al. ..... 600/509
5,987,519 A 11/1999 Peifer et al. ..... 709/230
6,026,008 A 2/2000 Feese ..... 365/63
6,038,469 A 3/2000 Karlsson et al. ..... 600/512
6,073,046 A 6/2000 Patel et al.
6,083,248 A 7/2000 Thompson ..... 607/30
6,088,608 A 7/2000 Schulman et al. ..... 600/345
6,093,146 A 7/2000 Filangeri ..... 600/300
6,101,478 A 8/2000 Brown ..... 705/2
6,102,856 A 8/2000 Groff et al.
6,154,674 A 11/2000 Meier ..... 607/23
6,160,478 A 12/2000 Jacobsen ..... 340/539
6,172,605 B1 1/2001 Matsumoto et al.
6,181,966 B1 1/2001 Nigam ..... 607/4
6,192,274 B1 2/2001 Worzewski ..... 607/14
6,225,901 B1 5/2001 Kail, IV ..... 340/539
6,245,092 B1 6/2001 Schaldach, Jr. ..... 607/1
6,263,243 B1 7/2001 Lang ..... 607/17
6,287,252 B1 9/2001 Lugo
6,366,871 B1 4/2002 Geva
6,466,793 B1 10/2002 Wallstedt et al. ..... 455/450
6,564,077 B2 5/2003 Mortara
6,694,177 B2 2/2004 Eggers et al.
6,697,655 B2 2/2004 Sueppel et al.
7,311,665 B2 12/2007 Hawthorne et al.
7,542,878 B2 6/2009 Nanikashvili
2002/0128804 A1 9/2002 Geva
2002/0143576 A1 10/2002 Nolvak et al. ..... 705/2
2003/0028442 A1 2/2003 Wagstaff et al.
2003/0069486 A1 4/2003 Sueppel et al.
2003/0069487 A1 4/2003 Mortara
2004/0010201 A1 1/2004 Korzinov et al.
2005/0119833 A1 6/2005 Nanikashvili
2005/0203349 A1 9/2005 Nanikashvili

FOREIGN PATENT DOCUMENTS

EP 0 484 880 11/1991
EP 0 834 846 1/1996
EP 0 811 959 6/1997
EP 1 072 994 1/2001
FR 2 787 905 12/1998
GB 2 285 135 6/1995
WO WO 94/13197 6/1994
WO WO 96/25877 8/1996
WO WO 97/00708 1/1997
WO WO 99/44494 9/1999
WO WO 00/30529 6/2000
WO WO 00/62663 10/2000

OTHER PUBLICATIONS

PCT International Search Report dated Aug. 21, 2002 in corresponding PCT application No. PCT/US02/12875, 4 pages.

United States Patent and Trademark Office Action mailed Mar. 13, 2006, U.S. Appl. No. 10/778,886, 14 pages.

European Patent Office EPO-Form 2001, Communication pursuant to Article 94(3) EPC dated May 14, 2008, Application No. 02 764 321.2-2319, 8 pages.
Reddie & Grose, Response to EPO Communication pursuant to Article 94(3) EPC dated May 14, 2008, filed Sep. 12, 2008, Application No. 02 764 321.2-2319, 10 pages.
Formalities Officer Martine Eich, European Patent Office EPO-Form 2004, Communication under Rule 71(3) EPC dated May 20, 2009, Application No. 02 764 321.2-2319, 20 pages.

* cited by examiner

CONTROL OF DATA TRANSMISSION BETWEEN A REMOTE MONITORING UNIT AND A CENTRAL UNIT

Matter enclosed in heavy brackets [ ] appears in the original patent but forms no part of this reissue specification; matter printed in italics indicates the additions made by reissue.

This invention relates to the transmission of data between a remote monitoring unit and a central unit, and more particularly to the optimization of such data transfer.

BACKGROUND OF THE INVENTION

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, an example being the heartbeat and its waveform.

Under prescribed conditions, the remote monitoring unit contacts a central unit to communicate information on the condition of the patient. For example, if the remote monitoring unit determines that the monitored physiological data suggests that the patient may be in distress or in an emergency, it may immediately and automatically transfer the monitored data to the central unit over a cellular telephone or comparable communications device. The central unit automatically, or in conjunction with medical personnel who are stationed at or are in contact with the central unit, analyzes the data and coordinates the provision of assistance to the patient when necessary. Where the analysis of the transmitted data indicates that there is no patient situation requiring immediate attention, the data is stored and may also be forwarded to the patient's physician so that treatments may be altered.

While operable, this approach may in some cases be wasteful of the battery power of the remote monitoring unit and require the expenditure of too much data transfer time over the cellular telephone system with its associated charges. The time of the medical personnel may also be used inefficiently.

There is a need for an improved approach for the control of data transfers between the remote monitoring unit and the central unit. The present invention fulfills this need, and further provides related advantages.

SUMMARY OF THE INVENTION

The present invention provides an approach for monitoring a patient and providing support to the patient. The present approach adopts a new data transfer architecture with improved selectivity of data transmission but retention of the data accumulation capability to build the patient history and also the emergency capability to assist the patient on an urgent basis when needed. The battery power of the remote monitoring unit is thereby used more judiciously, the cellular telephone connect time is reduced, and medical personnel time is better managed.

In accordance with the invention, a method of monitoring a patient comprises providing a monitoring apparatus including a remote monitoring unit associated with the patient. The remote monitoring unit includes a sensor that measures a physiological characteristic of the patient such as a cardiogram, a central unit, and a communications device which selectively establishes a communications link between the remote monitoring unit and the central unit. The remote monitoring unit obtains a monitored data set for the patient, analyzes the monitored data set to obtain a derived data set from the monitored data set, and determines from the derived data set that communication with the central unit is required. A communications link is established with the central unit, and the remote monitoring unit transmits to the central unit an initially transmitted data set related to the monitored data set. The central unit analyzes the initially transmitted data set and instructs the remote monitoring unit as to any additional transmitted data set, which may be related to the monitored data set, that is to be transmitted from the remote monitoring unit to the central unit and a time at which the additional transmitted data set is to be transmitted.

The present invention is therefore based in an architecture where the main body of data is not automatically transmitted from the remote monitoring unit to the central unit. That approach is likely to produce unnecessarily large and unnecessarily frequent data transfers which result in depletion of the batteries of the remote monitoring unit and large transmission-time costs. Instead, the central unit analyzes the initially transmitted data set, which is usually a reduced data set that is derived from or determined by the monitored data set, to determine whether a more complete data transfer in the form of the additional transmitted data set is required. If so, that transmission is made at a time specified by the central unit. The time of transmission may be immediate, as when an emergency condition is sensed, or deferred, as when the additional transmitted data set is needed for the patient history. The efficiency of communication is thereby optimized while at the same time meeting the medical requirements for the patient.

The step of the remote monitoring unit analyzing the monitored data set may be accomplished by comparing at least one element of the derived data set to a warning limit. The analysis of the initially transmitted data set may include obtaining a patient history from a memory, and analyzing the initially transmitted data set in relation to the patient history. The central unit may instruct the remote monitoring unit to transmit the additional transmitted data set substantially immediately or at a delayed time. The additional transmitted data set and the monitored data set may be the same or may not be the same data sets.

In one embodiment, the communications device comprises a radio frequency telephone terminal (such as a cellular or satellite telephone terminal) and a land-line telephone terminal. The radio frequency telephone connection may be made at any time, but the land-line telephone terminal is available only when the remote monitoring unit is physically connected to a land line. The transmission of the initially transmitted data set, which usually is a much smaller amount of data than the monitored data set, may be made over the radio frequency telephone connection. Upon analysis at the central unit, if there appears to be the possibility of an emergency wherein more data is needed immediately, the larger additional transmitted data set may be immediately transmitted over the radio frequency telephone connection. On the other hand, where the central unit determines that there is not an emergency but that it would be useful to have the additional transmitted data set for future reference as a part of the patient history, the central monitoring unit may instruct the remote monitoring unit to store and then transmit the additional transmitted data set at a later time over the land-line telephone terminal when such a connection is available or the radio frequency telephone connection when transmission costs are lower (i.e., off-peak hours).

This selective transmission approach, wherein data transmission from the remote monitoring unit is not automatic but instead is under control of the central unit, reduces the amount of data that must be transmitted over a cellular telephone connection or similar expensive communication device. This selectivity reduces cellular telephone connect time and charges to the user, and also may significantly increase the lifetime of the remote monitoring unit between battery charging, because establishing and maintaining the cell phone connection constitutes a significant portion of the battery usage of the remote monitoring unit. The human resources of the medical personnel at or in communication with the central unit are also better utilized. Only those situations that are more likely to be actual emergencies are brought to the attention of those medical personnel, so that they have more time for such potential actual emergencies.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
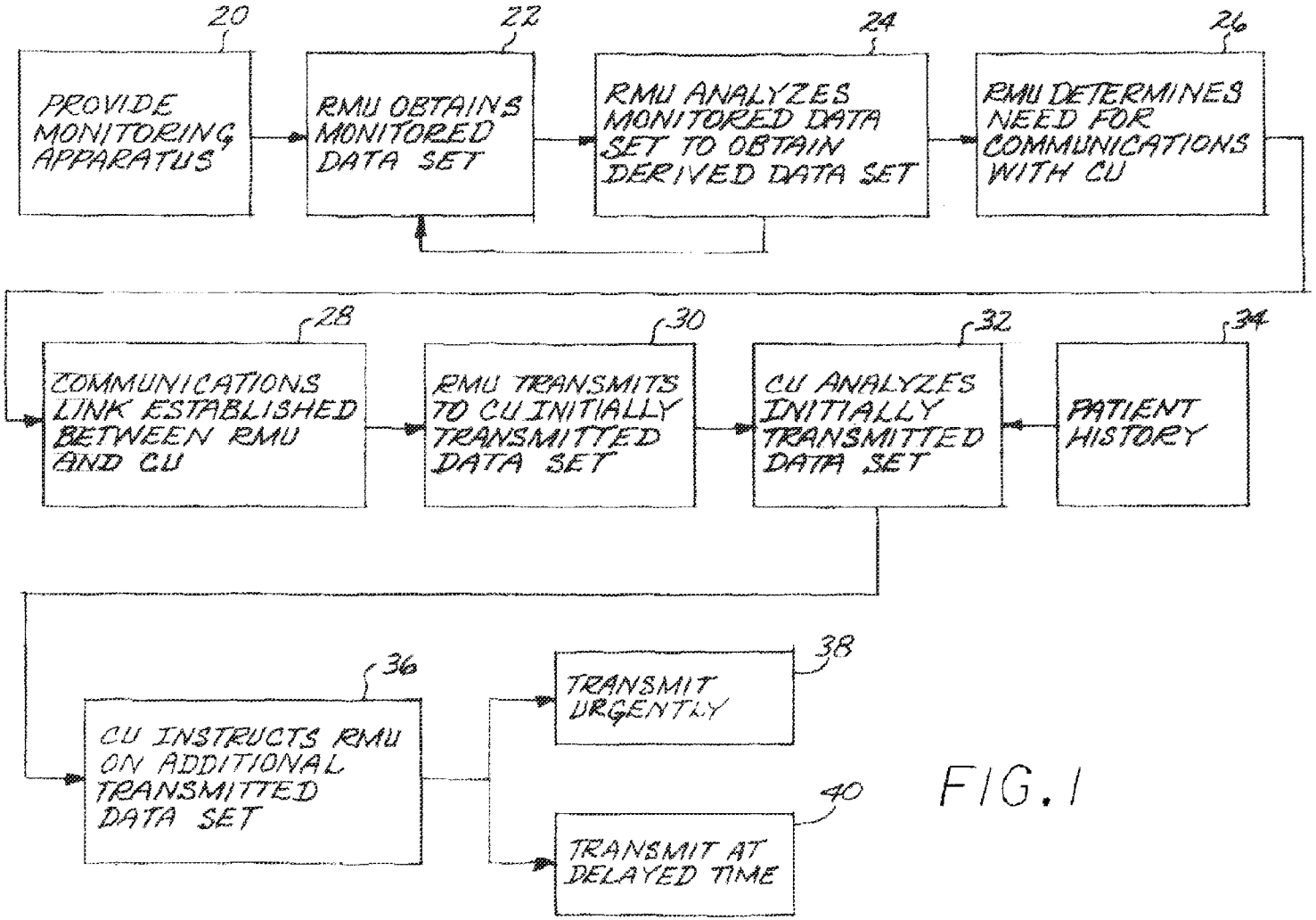
FIG. 1 is a block flow diagram of a method for practicing the present invention.
Figure 2:
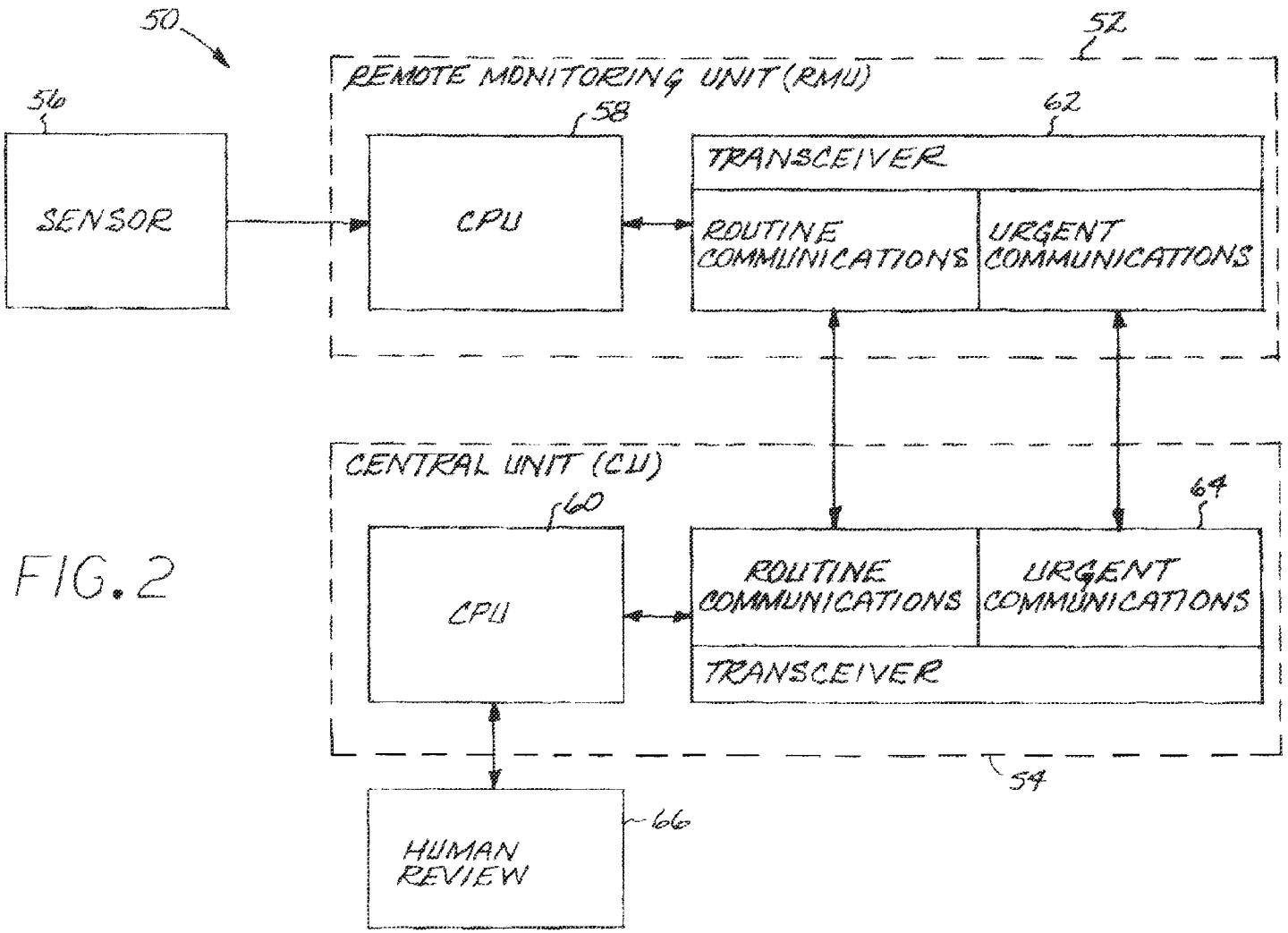
FIG. 2 is a simplified schematic block diagram of a preferred apparatus with which the present invention may be used.

FIG. 1 depicts an approach for practicing the present invention. A monitoring apparatus is provided, numeral 20. The monitoring apparatus may be of any operable form, and one preferred form of the monitoring apparatus 50 is illustrated in FIG. 2. The monitoring apparatus 50 is shown in a simplified form illustrating only those portions that are required to discuss the present invention. More detail of a monitoring apparatus may be found in U.S. Pat. No. 5,959,529, whose disclosure is incorporated by reference.

The monitoring apparatus 50 includes a remote monitoring unit (RMU) 52 carried by an ambulatory patient, and a central unit (CU) 54. The central unit 54 may be a single computer, but it is more typically a file server or a network. Other remote monitoring units, that are not "portable" in the sense that they are not carried on the person of the patient but may be at a fixed location in a patient's home or hospital facility, may be used as well. A sensor 56 measures a physiological characteristic of a patient, and is typically in contact with the patient. ("Patient" is used in a broad sense, and refers to a person being monitored.) There may be one sensor or more than one sensor 56, depending upon the parameters of the patient that are of interest. Examples of operable sensors 56 include a heart monitor sensor, a blood pressure monitor sensor, a temperature monitor sensor, a respiration sensor, a brain wave sensor, a blood chemistry sensor such as a blood glucose sensor or a blood oxygen sensor, a patient position sensor, and a patient activity sensor. Sensors of various types are known in the art, and details of their construction and operation do not form a part of the present invention.

In either event, the sensor 56 is in communication with a central processing unit (CPU) 58 of the remote monitoring unit 52, with intermediate signal conditioning equipment as necessary (not shown here). The central processing unit 58 performs analyses of the signals of the sensor 56, as will be discussed subsequently. Similarly, the central unit 54 includes a central processing unit (CPU) 60 to perform calculations and analyses, as will be discussed subsequently. (As noted, the central unit 54 and its CPU 60 may be of any operable type, such as a dedicated system, a network, or a file server. Each CPU 58 and 60 typically includes a microprocessor.)

The remote monitoring unit 52 and the central unit 54 may be placed in two-way communication with each other through a transceiver 62 located in the remote monitoring unit 52 and a communicating transceiver 64 located in the central unit 54. (The description that the transceiver is "in" the described device includes the case where the transceiver is not physically within the same structure as the CPU, but is instead in another location but in communication with the CPU. Thus, for example, the central unit 54 may include a file server in which the CPU 60 is located and a physically separate cellular transceiver 64 with a communication link to the file server and the CPU 60.) The transceivers 62, 64 may include any operable type of communications devices. For example, they may include a modem to establish communications over a conventional land line for routine communications. They may also include a cellular telephone transceiver to establish communications on an urgent or routine basis. The transceivers 62, 64 may also be equipped for two-way voice communication between the patient and a person at the central unit 54. The transceivers 62, 64 may interconnect over the internet, with or without land line or cellular links at each end, as well, with the internet having its own communications capabilities. The present invention is concerned in part with determining how much data should be transmitted as urgent communications and how much data should be transmitted as routine communications. The central unit 54 is provided with an interface to allow human review 66 of recommended actions of the central processing unit 60, as by the patient's physician.

Returning to the discussion of FIG. 1, the remote monitoring unit 52 obtains a monitored data set for the patient using the sensor(s) 56, numeral 22. The monitored data set is often fairly voluminous, such as a continuous loop of 24 hours of a cardiograph of the patient in the form of (voltage, time) data pairs.

The remote monitoring unit 52 analyzes the monitored data set to obtain a derived data set from the monitored data set, numeral 24. The derived data set is typically much smaller in size than the monitored data set, and includes types of data that have been previously found to be significant. The derived data set may include, for example, an indication of a specified type of an abnormal heart beat (i.e., a code for the sensed abnormality), a heart rate (number of beats per minute), maximum voltage value, basic waveshape assessment, and whether patient-specific criteria were violated by the heartbeat waveform. The derived data set is obtained from the monitored data set by conventional waveform processing procedures.

The central processing unit 58 of the remote monitoring unit 52 analyzes the derived data set, typically by comparing the values of the parameters with warning limits previously determined for the patient and provided to the remote monitoring unit 52 or by other suitable approaches. For example, if the heart rate exceeds a heart rate warning limit, the maximum voltage value is greater than a voltage warning limit, and/or the wave shape is not within a waveshape warning limit, the remote monitoring unit 52 may determine that there is a potential emergency with the patient or that data should be transmitted immediately for diagnostic purposes. In that event, the remote monitoring unit 52 determines that communication with the central unit 54 is required immediately, numeral 26. The remote monitoring unit 52 may instead determine that the data is of interest for inclusion in the patient's centrally stored history, but that there is no emergency at hand. In that case, the data of interest is marked for transmission at a later time, as in a daily routine transmission. The remote monitoring unit 52 may instead determine that the data is of no particular interest. In the majority of situations there is no potential emergency and communications are not required, and the monitoring apparatus then cycles from step 24 back to step 22 and repeats steps 22 and 24.

Where it has been determined that communication is required immediately, a communications link is immediately established through the transceivers 62, 64 between the remote monitoring unit 52 and the central unit 54, numeral 28. If it is not possible to establish communications through a land line, then there is an attempt to establish the more expensive and less dependable radio frequency cellular link.

The remote monitoring unit 52 transmits to the central unit 54 an initially transmitted data set, numeral 30. The initially transmitted data set may be related to the monitored data set or unrelated to the monitored data set (as for example information suggesting a sensor failure), the former being the most common. The initially transmitted data set may be the same as the derived data set, or it may include different data. For example, the initially transmitted data set may also include information from other sensors, such as a respiration rate or blood pressure of the patient. The initially transmitted data set is structured to contain the most significant information for decision making and to permit transmission to the central unit 54 in a relatively short time. The central unit 54 therefore has the most significant information needed for further decision making concisely.

The central processing unit 60 of the central unit 54 analyzes the initially transmitted data set, numeral 32. In performing this analysis, the central unit 54 often relies on patient history (numeral 34) that is stored in the central unit 54 or is obtainable by a further link to the doctor or hospital that is responsible for the patient. The central unit 54 may be aided in its decision making by human review and consideration of the situation, numeral 66 of FIG. 2. The human review 66 may be conducted by a medical technician or by the patient's physician. However, at this stage it is preferred that the analysis step 32 be as fully automated as possible so that a decision may be made quickly regarding the need for further information. The analysis and human review at this point are not performed for the purposes of diagnosis, but instead to determine whether more information is required immediately from the remote monitoring unit 52.

From the information provided to it by the initially transmitted data set and from other sources such as the patient history, the central unit 54 determines the subsequent flow of information from the remote monitoring unit 52 and instructs the remote monitoring unit 52 as appropriate, numeral 36. The central unit 54 may, for example, determine that no further information need be transmitted, may determine that more information in the form of an additional transmitted data set is required on an urgent basis, or may determine that more information in the form of the additional transmitted data set is required at a later time. The volume and type of data to be transmitted is also determined. In the case where no further information is required, the communication between the remote monitoring unit 52 and the central unit 54 may be immediately terminated, and the remote monitoring unit 52 cycles back to step 22. In the case where further information is required on an urgent basis, the communication link remains open and the additional transmitted data set is transmitted from the remote monitoring unit 52 to the central unit 54 immediately, numeral 38. In the case where further information is required at a later time such as at the time of routine data transmissions, the communication link is terminated as far as the urgent communication is concerned but the data of interest is marked for later transmission. At a later delayed time, such as at the time of routine data transmissions for the day, the additional transmitted data is transmitted from the remote monitoring unit 52 to the central unit, numeral 40. In a typical case, the additional transmitted information is transmitted with routine transmissions using a telephone land line, which is substantially less expensive than using a cellular telephone link and also is accomplished when the remote monitoring unit is receiving line power so that there is no battery drain. The additional transmitted data set selected by the central unit 54 may include the monitored data set, less than the full monitored data set, or more than the monitored data set because, for example, additional information from other sensors is required.

An example is helpful in illuminating the role of the central unit. If the doctor in charge of the patient has instructed that fewer than three premature ventricular contraction (PVC) events per hour is not of concern, but that three or more events per hour is of sufficient concern to require more information on an urgent basis, the remote monitoring unit 52 contacts the central unit upon the occurrence of each such event. The central unit 54 consults the patient history, which contains a running listing of the occurrence of such events. If the present event is found to be the third event in the last hour, then the central unit 54 instructs the remote monitoring unit 52 to transmit the additional transmitted data set on an urgent basis. If the present event does not result in a condition of three or more events in the last hour, it still may be desirable to transmit the waveform for the event and the adjacent time periods for the patient history but only at the next routine transmission. (Alternatively, the PVC count may be maintained by the remote monitoring unit 52, and contact established with the central unit 54 only when three PVC events are counted in any one-hour period.)

The advantages of the present approach are illustrated in another example. By making decisions based on the initially transmitted data set, it may be necessary to maintain a cellular connection for at most a minute. On the other hand, if the entire monitored data set were automatically transmitted from the remote monitoring unit 52 to the central unit 54, the time required might be on the order of several minutes of cellular connection time to transmit each 5 minutes of the cardiogram. This connection results in a significant drain on the battery of the remote monitoring unit and extra cellular connection time and cost, which are to be avoided if possible. Where it is judged that there is an urgent need for the additional transmitted data set because the patient may be in danger or the data is of immediate diagnostic value, the cellular link is maintained and the full additional transmitted data set is communicated as necessary so that the patient may be aided.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method of monitoring a patient, comprising the steps of providing a monitoring apparatus including a remote monitoring unit associated with the patient, the remote monitoring unit including a sensor that measures a physiological characteristic of the patient, a central unit, and a communications device which selectively establishes a communications link between the remote monitoring unit and the central unit;

the remote monitoring unit obtaining a monitored data set for the patient;

the remote monitoring unit analyzing the monitored data set to obtain a derived data set from the monitored data set;

the remote monitoring unit determining from the derived data set that communication with the central unit is required;

establishing a communications link with the central unit;

the remote monitoring unit transmitting to the central unit an initially transmitted data set related to the monitored data set;

the central unit analyzing the initially transmitted data set *to determine whether an additional data set related to the monitored data set is required to be transmitted by the remote monitoring unit*; and the central unit, *when the additional data set related to the monitored data set is required,* instructing the remote monitoring unit [as to any] *that the* additional [transmitted] data set related to the monitored data set [that] is to be transmitted from the remote monitoring unit to the central unit and *as to* a time at which the additional [transmitted] data set is to be transmitted based on the [condition sensed] *initially transmitted data set received from the remote monitoring unit*.

2. The method of claim 1, wherein the monitored data set comprises a cardiogram of the patient.

3. The method of claim 1, wherein the step of the remote monitoring unit analyzing the monitored data set includes the step of comparing at least one element of the derived data set to a warning limit.

4. The method of claim 1, wherein the step of the central unit instructing the remote monitoring unit *as to a time* includes the step of the central unit instructing the remote monitoring unit to transmit the additional [transmitted] data set substantially immediately.

5. The method of claim 1, wherein the step of the central unit instructing the remote monitoring unit *as to a time* includes the step of the central unit instructing the remote monitoring unit to transmit the additional [transmitted] data set at a delayed time.

6. The method of claim 1, wherein the additional [transmitted] data set and the monitored data set are not the same.

7. The method of claim 1, wherein the step of the central unit analyzing the initially transmitted data set includes the step of the central unit obtaining a patient history from a memory, and analyzing the initially transmitted data set in relation to the patient history.

8. The method of claim 1, wherein the communications device comprises a radio frequency telephone terminal and a land-line telephone terminal.

9. A method of monitoring a patient, comprising the steps of providing a monitoring apparatus including a remote monitoring unit associated with the patient, a central unit, and a communications device which selectively establishes a communications link between the remote monitoring unit and the central unit;

the remote monitoring unit obtaining a monitored data set for the patient;

the remote monitoring unit establishing a communications link with the central unit;

the remote monitoring unit transmitting to the central unit an initially transmitted data set related to the monitored data set;

the central unit analyzing the initially transmitted data set *to determine whether an additional data set related to the monitored data set is required to be transmitted by the remote monitoring unit*;

the central unit, *when the additional data set related to the monitored data set is required,* instructing the remote monitoring unit [as to an] *that the* additional [transmitted] data set [that] is to be transmitted from the remote monitoring unit to the central unit and *instructing as to* a time at which the additional [transmitted] data set is to be transmitted; and the remote monitoring unit transmitting the additional [transmitted] data set to the central unit at the time instructed by the central unit based on the [condition sensed] *initially transmitted data set received from the remote monitoring unit*.

[10. The method of claim 9, wherein at least a part of the additional transmitted data set is related to the monitored data set.]

11. The method of claim 9, wherein the monitored data set comprises a cardiogram of the patient.

12. The method of claim 9, wherein the step of the central unit instructing the remote monitoring unit *as to a time* includes the step of the central unit instructing the remote monitoring unit to transmit the additional transmitted data set substantially immediately.

13. The method of claim 9, wherein the step of the central unit instructing the remote monitoring unit *as to a time* includes the step of the central unit instructing the remote monitoring unit to transmit the additional transmitted data set at a delayed time.

14. The method of claim 9, wherein the additional transmitted data set and the monitored data set are not the same.

15. The method of claim 9, wherein the step of the central unit analyzing the initially transmitted data set includes the step of the central unit obtaining a patient history from a memory, and the central unit analyzing the initially transmitted data set in relation to the patient history.

16. A method of monitoring a patient, comprising the steps of providing a monitoring apparatus including a remote monitoring unit associated with the patient, the remote monitoring unit including a sensor that measures a physiological characteristic of the patient, a central unit, and a communications device which selectively establishes a communications link between the remote monitoring unit and the central unit;

the remote monitoring unit obtaining a monitored data set for the patient;

the remote monitoring unit analyzing the monitored data set to obtain a derived data set from the monitored data set;

the remote monitoring unit determining from the derived data set that communication with the central unit is required;

establishing a communications link with the central unit;

the remote monitoring unit transmitting to the central unit an initially transmitted data set related to the monitored data set;

the central unit analyzing the initially transmitted data set *to determine whether an additional data set related to the monitored data set is required to be transmitted by the remote monitoring unit*; and the central unit instructing the remote monitoring unit [as to any] *that the* additional [transmitted] data set related to the monitored data set [that] is to be transmitted from the remote monitoring unit to the central unit and *as to* a time at which the additional [transmitted] data set is to be transmitted based on the step of the central unit analyzing the initially transmitted data set.

17. A method of monitoring a patient, comprising the steps of providing a monitoring apparatus including a remote monitoring unit associated with the patient, the remote monitoring unit including a sensor that measures a physiological characteristic of the patient, a central unit, and a communications device which selectively establishes a communications link between the remote monitoring unit and the central unit based on [to] *a* condition sensed;

the remote monitoring unit obtaining a monitored data set for the patient;

the remote monitoring unit analyzing the monitored data set to obtain a derived data set from the monitored data set;

the remote monitoring unit determining from the derived data set that communication with the central unit is required;

establishing a communications link with the central unit;

the remote monitoring unit transmitting to the central unit an initially transmitted data set related to the monitored data set;

the central unit analyzing the initially transmitted data set *to determine whether an additional data set related to the monitored data set is required to be transmitted by the remote monitoring unit*; and the central unit instructing the remote monitoring unit [as to any] *that the* additional [transmitted] data set related to the monitored data set [that] is to be transmitted from the remote monitoring unit to the central unit and *as to* a time at which the additional [transmitted] data set is to be transmitted *based on the condition sensed*.

18. A method of monitoring a patient, comprising the steps of providing a monitoring apparatus including a remote monitoring unit associated [wit] *with* the patient, the remote monitoring unit including a sensor that measures a physiological characteristic of the patient, a central unit, and a communications device which selectively establishes a communications link between the remote monitoring unit and the central unit;

the remote monitoring unit obtaining a monitored data set for the patient;

the remote monitoring unit analyzing the monitored data set to obtain a derived data set from the monitored data set;

the remote monitoring unit determining from the derived data set that communication with the central unit is required based upon [the] *a* condition sensed;

establishing a communications link with the central unit;

the remote monitoring unit transmitting to the central unit an initially transmitted data set related to the monitored data set;

the central unit analyzing the initially transmitted data set *to determine whether an additional data set related to the monitored data set is required to be transmitted by the remote monitoring unit*; and the central unit, *when the additional data set related to the monitored data set is required,* instructing the remote monitoring unit [as to any] *that the* additional [transmitted] data set related to the monitored data set [that] is to be transmitted from the remote monitoring unit to the central unit and *as to* a time at which the additional [transmitted] data set is to be transmitted.

*19. The method of claim 1, further comprising, when the additional data set related to the monitored data set is required, the central unit determining whether the additional data set related to the monitored data set is required to be transmitted by the monitoring unit immediately or at a later time.*

*20. The method of claim 9, further comprising the central unit further determining whether the additional data set related to the monitored data set is required to be transmitted by the monitoring unit immediately or at a later time.*

*21. The method of claim 16 wherein analyzing the initially transmitted data set to determine whether an additional data set related to the monitored data set is required to be transmitted by the remote monitoring unit further comprises determining, based at least on a personal history of the patient, whether the additional data set related to the monitored data set is required to be transmitted by the remote monitoring unit.*

*22. The method of claim 16, further comprising, when the additional data set related to the monitored data set is required, determining whether the additional data set related to the monitored data set is required to be transmitted by the monitoring unit immediately or at a later time.*

*23. The method of claim 17, wherein analyzing the intially transmitted data set to determine whether an additional data set related to the monitored data set is required to be transmitted by the remote monitoring unit further comprises determining, based at least on a personal history of the patient, whether the additional data set related to the monitored data set is required to be transmitted by the remote monitoring unit.*

*24. The method of claim 17, further comprising, when the additional data set related to the monitored data set is required, determining whether the additional data set related to the monitored data set is required to be transmitted by the monitoring unit immediately or at a later time.*

*25. The method of claim 18, wherein analyzing the intially transmitted data set to determine whether an additional data set related to the monitored data set is required to be transmitted by the remote monitoring unit further comprises determining, based at least on a personal history of the patient, whether an additional data set related to the monitored data set is required to be transmitted by the remote monitoring unit.*

*26. The method of claim 18, further comprising, when the additional data set related to the monitored data set is required, determining whether the additional data set related to the monitored data set is required to be transmitted by the monitoring unit immediately or at a later time.*

* * * * *

UNITED STATES PATENT AND TRADEMARK OFFICE

CERTIFICATE OF CORRECTION

PATENT NO. : RE43,767 E
APPLICATION NO. : 12/774026
DATED : October 23, 2012
INVENTOR(S) : Philip N. Eggers and Lon M. Severe It is certified that error appears in the above-identified patent and that said Letters Patent is hereby corrected as shown below:

On the title page, item [75]; Line 1: delete "Satl Lake City" and insert -- Salt Lake City --, therefor.

Page 8, Column 10, Line 39: delete "intially" and insert -- initially --, therefor.
Page 8, Column 10, Line 52: delete "intially" and insert -- initially --, therefor.

Signed and Sealed this
Nineteenth Day of March, 2013

Teresa Stanek Rea
*Acting Director of the United States Patent and Trademark Office*